United States Patent [19]

Brown

[11] Patent Number: 4,918,229

[45] Date of Patent: Apr. 17, 1990

[54] METHOD OF PRODUCING PRIMARY AMINES IN HIGH YIELDS AND NOVEL INTERMEDIATES THEREFOR

[75] Inventor: Herbert C. Brown, West Lafayette, Ind.

[73] Assignee: Aldrich Chemical Company, Inc., Milwaukee, Wis.

[21] Appl. No.: 226,080

[22] Filed: Jul. 29, 1988

[51] Int. Cl.$^4$ .............................................. C07C 82/00
[52] U.S. Cl. .................................................. 564/302
[58] Field of Search ........................................ 564/302

[56] References Cited

PUBLICATIONS

Chemical Abstracts; vol. 104, (1986), #130058b; Jadhav et al.

Primary Examiner—Joseph A. Lipovsky
Attorney, Agent, or Firm—Niblack & Niblack

[57] ABSTRACT

A novel process for producing hindered and unhindered primary amines represented by the formula $RNH_2$ and $R*NH_2$ in high yields from novel intermediates $RBMe_2$ or $R*BMBe_2$ wherein R is an organo group, R* is a chiral organo group attached to boron, B is boron and Me is methyl.

7 Claims, No Drawings

METHOD OF PRODUCING PRIMARY AMINES IN HIGH YIELDS AND NOVEL INTERMEDIATES THEREFOR

BACKGROUND OF THE INVENTION

A. Technical Field

This invention relates to the synthesis of primary amines including optically active primary amines, and more particularly to improved processes for producing such primary amines from olefins and boronic esters, and to novel intermediates useful therein.

Optically active primary amines are of major biological and synthetic importance. For example, (R)-(−)-sec-butylamine is present in pharmacologically active species such as β-blockers and CNS analgesics.

In the typical synthesis of primary amines, $RNH_2$ from organoboranes, one organic group is typically lost as boronic acid which results in a maximum yield of 67% for less hindered R groups and 50% for more hindered R groups. Accordingly, there has been a longstanding need for methods which provide a more efficient transfer of organyl groups from boron to nitrogen. The present invention provides such intermediates and methodologies.

B. Prior Art

Organoboranes have been used to synthesize amines by reaction with appropriate aminating reagents such as $NH_2Cl$ and $NH_2OSO_3H$ [H. C. Brown, W. R. Heydkamp, E, Breuer, W. S. Murphy, *J. Am. Chem. Soc.* 1964, 86, 3365]; $NH_3+NaOCl$ [G. W. Kabalka, K. A. Sastry, G. W. McCollum, H. Yoshioka, *J. Org. Chem.* 1981, 46, 4296]; chloramine-T [V. B. Jigajinni, A. Pelter, K. Smith, *Tetrahedron Letters* 1978, 181] and O-mesitylenesulfonylhydroxylamine [Y. Tamura, J. Minamikawa, S. Fujii, M. Ikeda, *Synthesis* 1973, 196].

As mentioned above, yields achieved in these prior art processes were, at most, 67% for less hindered R groups and 50% for more hindered R groups.

The reaction of trialkylboranes with freshly prepared chloramine proceeds in the presence of aqueous sodium hydroxide. However, only two of the three groups in $R_3B$ were utilized.

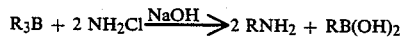

Consequently the maximum possible yield for $R_3B$ is only 67%. H. C. Brown, W. R. Heydkamp, E. Breur and W. S. Murphy, *J. Am. Chem. Soc.*, 86, 3365 (1964).

More hindered alkenes undergo hydroboration only to the dialkylborane stage, readily converted into the corresponding dialkylborinic acids or esters. These derivatives also react with preformed chloramine to form the primary amines. But in this case, only one of the two groups could be made to react.

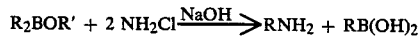

Consequently, in such cases, the maximum yield is only 50%. Moreover, the reaction of the more hindered dialkylborane derivative is very sluggish with decreased yields. H. C. Brown, G. W. Kramer, A. B. Levy and M. M. Midland, "Organic Synthesis via Boranes", Wiley-Interscience, New York, 1975.

The preparation of optically active primary amines of very high anantiomeric purities from boronic esters of essentially 100% optical purity and LiMe was described by Herbert C. Brown et al, *J. Am. Chem. Soc.* 1986, 108, 6761–6764. This procedure produced optically pure primary amines in yields of between 72–83%. While improved yields were obtained on a laboratory scale, methyllithium is a relatively expensive reagent, and is too expensive to be used for large scale commercial production of amines. Thus a need remains for a process for economically producing primary amines in high yields as well as for economically producing optically active amines of high optical purity in improved yields.

The present invention provides a process which enables synthesis of both hindered and unhindered primary amines in excellent yields of up to 95%., and in all cases, in higher yields than those achieved by prior art methods.

SUMMARY OF THE DISCLOSURE

In one embodiment, the present invention provides a simple procedure for converting olefins such as alkenes into the corresponding primary amine by reacting the appropriate dimethylborane, prepared from the desired olefin and dimethylborohydride, with a suitable aminating agent according to the following reaction scheme:

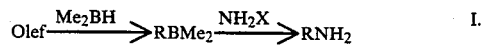

In another embodiment, optically active primary amines are prepared from optically pure $R^*BIpc_2$ according to the following reaction scheme:

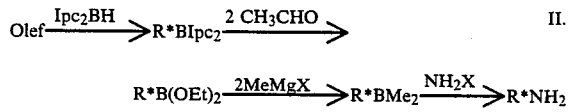

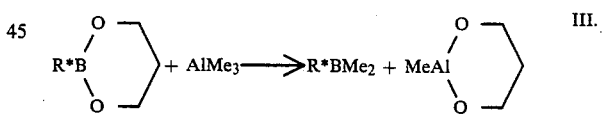

Alternatively, trimethylaluminum, $AlMe_3$, can be substituted for the methyl Grignard reagent in nonethereal solvents. A representative reaction with a trimethylene glycol ester is shown below.

$$R^*B\begin{matrix}O\\\\O\end{matrix}\Big\rangle + AlMe_3 \longrightarrow R^*BMe_2 + MeAl\begin{matrix}O\\\\O\end{matrix}\Big\rangle \qquad III.$$

The present invention also provides novel intermediates represented by the formula $RBMe_2$ and $R^*BMe_2$ wherein R is an organo group and R* is a chiral organo group.

As used herein, the term "organo" refers to organyl groups having up to 30 carbon atoms. The process is broadly applicable to any organyl group, substituted or unsubstituted, i.e., alkyl, cycloalkyl, heterocyclic, steroidal, etc. commonly found in pharmaceutically active primary amines $RNH_2$ or $R^*NH_2$. Such pharmaceutically active primary amines and intermediates and reagents for producing pharmaceutically or agriculturally active amines which may be prepared by the process of this invention include, but are not limited to: 2-diphenylmethylenebutylamine (Etifelmin), 3,4-dihydroxyphenethylamine (Dopamine), 3-α-amino-20-oxo-5-pregnane (Funtimine), 1-H-imidazole-4-ethaneamine (Ibrotamine), 3-(10,11-dihydro-5H-dibenzo[a,d]-cycloheptene-5-ylidene)-N,N-dimethyl-1-propaneamine (Amitriptyline), 2-thiazolamine (2-aminothiazole), 2-pyridineamine (2-aminopyridine), 4-methyl-2-thiazolamine (Normotiroide), cyclohexylamine, O-3-amino-3-deoxy-α-D-glucopyranosyl-(1→6)-0-[2,6-diamino-2,3,4,6-tetradeoxy-α-D-erythrohexopyranosyl-(1→4)]-2-deoxy-D-streptamine (Dibekacin), p,α-dimethylphenylethylamine (Aptrol), p-fluorobenzenamine (p-fluoroanaline), α,α-dimethylphenylethylamine (Phentermine), 3,6-acridinediamine (Proflavine), and the like.

While there are alternative methods for producing the key intermediates, $RBMe_2$ and $R*BMe_2$, the process of this invention comprises producing either a primary amine or an optically active primary amine from the appropriate organodimethylborane to obtain excellent yields of the desired amine. This primary amine synthesis from organoborane intermediates provides a novel method of introducing an amine functionality into olefins in a regio- and stereoselective manner as illustrated below.

Accordingly, one aspect of the invention comprises a process for producing primary amines represented by the formula $R*NH_2$ or $RNH_2$ from $R+BMe_2$ or $RBMe_2$, respectively, wherein $R*$ is an optically active $[(+)$ or $(-)]$ substituted or unsubstituted, cyclic or acyclic organo group, and R is the same achiral organo group. The term "chiral" is used herein, refers to compounds which lack reflection symmetry, i.e. are not identical with their mirror images. The term "achiral" refers to compounds which possess reflection symmetry.

In another embodiment, the present invention provides novel intermediates useful in the preparation of chiral primary amines of essentially 100% ee (ee=enantiomeric excess) represented by the formula $R*BMe_2$ and as well as a novel process for producing said intermediates wherein $R*$ is a chiral organo group having up to 30 carbon atoms.

The term essentially 100% ee refers to an enantiomeric excess of at least 95% of one of the members of an enantiomeric pair.

The term "enantiomeric pair" refers to a pair of substances whose molecules are non-identical mirror images.

The improved process for preparing chiral primary amines, $R*NH_2$ in high yields generally comprises heating a dimethylalkylborane, $R*BMe_2$, wherein $R*$ is a chiral organyl group, in a suitable solvent or solvents with an aminating agent, preferably O-hydroxylamine sulfonic acid, treating the reaction with aqueous base to liberate the primary amine, and isolation of same by distillation, or crystallization, or as the hydrochloride by treatment with ethereal HCl.

The intermediate dimethylalkylboranes, $R*BMe_2$ are prepared by reacting a boronic ester $R*B(OEt)_2$ with Grignard reagent, MeMgX. The boronic esters may be conveniently prepared by the procedure described by H. S. Brown, B. Singaram, *J. Am. Chem. Soc.*, 106 1797 (1984).

As used herein, the term "alkyl" refers to a substituted or unsubstituted, cyclic, polycyclic, or acyclic (straight or branched chain) alkyl group of from 3 to 30 carbon atoms.

The process is broadly applicable to R=any organyl group, i.e. alkyl, aryl, heterocyclic, steroidal, commonly found in pharmaceutically active amines.

The term "organyl", as used herein, refers to an aliphatic, alicyclic, steroidal or heterocyclic organic group.

DETAILED DESCRIPTION OF PREFERRED EMBODIMENTS

The following examples further illustrate the present invention. All operations were initially carried out under a nitrogen atmosphere with oven-dried glassware. The spectra were obtained in an inert atmosphere. The $^{11}$BNMR spectra were recorded on a Varian FT-80A spectrometer and the chemical shifts are in δ relative to the ethyl etherate of boron trifluoride, $EE.BF_3$ with chemical shifts downfield from $EE.BF_3$ assigned as positive. The $^1$H NMR spectra were scanned on a Varian T-60 spectrometer, and the $^{13}$C NMR spectra were obtained on a Varian FT-80 instrument. Chemical shifts, all in $D_2O$, are relative to external $Me_4Si$ for $^1$H and $^{13}$C NMR spectra. Gas chromatographic analyses were carried out with a Varian 1400 FID instrument equipped with a Hewlett-Packard 3390A integrator/plotter using a 6 ft×0.125 in. column of 10% Carbowax 20M-2%KOH on Chromosorb W and an internal standard. Capillary gas chromatographic analyses were carried out with a Hewlett-Packard 5890 chromatograph. Optical rotations were measured on a Rudolph Polarimeter Autopol III. Unless otherwise indicated, optical rotations were measured at 20° C. Melting points are uncorrected.

Tetrahydrofuran (THF) was distilled from sodium benzophenone ketyl. Anydrous diethyl ether (EE) was purchased from Mallincrodt, Inc. and was used directly. Hydroxylamine-O-sulfonic acid was obtained from Aldrich Chemical Co. and used as such. The boronic esters were prepared by the procedures described by Brown, H. C. et al., *J. Am. Chem. Soc.*, 1986, 107, 4980.

EXAMPLE 1

Preparation of Trans-2-methylcyclopentylamine

A 50-mL centrifuge vial fitted with a rubber septum and magnetic stirring bar was charged with 5.6 mL of a 1.8M diethyl ether solution of lithium dimethylborohydride (10 mmol) and 1.1 mL of 1-methylcyclopentene (10.4 mmol) and cooled to 0° C. Neat chlorotrimethylsilane (1.3 mL, 10.2 mmol) was added with stirring. The reaction mixture was then stirred at 25° C. for 4 h. The $^{11}$B NMR spectrum of the reaction mixture showed a signal at δ+86 due to the clean formation of the trialkylborane. The reaction mixture was centrifuged and the clear supernatant liquid was transferred via a double-ended needle to a 50-mL flask. The lithium chloride was washed with 2 mL of diethyl ether and the washing combined with the supernatant solution. The trialkylborane solution was diluted with 10 mL of tetrahydrofuran and hydroxylamine-O-sulfonic acid (2.26 g, 20 mmol) was added using a solid addition tube. Initial exothermic reaction was controlled by the rate of addition of HSA and by water bath cooling. The reaction mixture was stirred at 25° C. for 12 h and water (10 mL) was added. The $^{11}$B NMR spectrum of the organic layer showed a peak at δ+31 due to the formation of boronic acid derivative. The reaction mixture was extracted with diethyl ether (20 mL) and the acidic aqueous layer was separated.

The aqueous phase was cooled to 0° C., diethyl ether (20 mL) and n-dodecane (1.022 g, 6 mmol) was added and the reaction mixture was made strongly alkaline by adding aqueous NaOH (17M, 4 mL) with stirring. The organic phase was separated and the aqueous phase was extracted again with diethyl ether (20 mL). The combined organic phase was dried over anhydrous MgSO$_4$ and an aliquot was withdrawn for GC analysis. The diethyl ether solution of the amine was reacted with ethereal HCl (2M, 6 mL) to precipitate the amine at its hydrochloride. The solid thus obtained was isolated, washed with diethyl ether (5×2 mL) and dried (25° C., 12 torr) to yield 1.1 g (81%, 99% ee): mp 182°–186° C.

EXAMPLES 2–11

The following illustrative compounds were prepared following the procedure of Example 1:

n-Octylamine hydrochloride, mp 201°–206° C., 85% yield, 99% ee, from 1-octene. Literature yields of this product range from 27% (from R$_3$B, chloroamine-T), 32% (from R$_3$B, in situ chloramine) and 69% (from R$_3$B or R$_2$BOR' and HSA).

2-Methyl-1-pentylamine hydrochloride, mp 140°–142° C., 95% yield, 99% ee, from 2-methyl-1-pentene. Reported literature yields of this product range from 24% (from R$_3$B, in situ chloramine) to 58% (R$_3$B or R$_2$BOR'/chloramine).

2-Butylamine hydrochloride, m.p. 138°–140° C., 95% yield, 99% ee, from cis-2-butene.

3-Hexylamine hydrochloride, mp 228°–230° C., 92% yield, 99% ee, from cis-hexene. Reported literature yields of this product range from 48 to 52% (from R$_3$B or R$_2$BOR'/HSA or chloroamine).

exo-2-Norbornylamine hydrochloride, mp 208° C. (dec), 99% yield, 99% ee, from 2-norbornene. Reported literature yields of this product, 24% from R$_3$B and in situ chloramine.

Cyclohexylamine hydrochloride, 94% yield, 99% ee, from cyclohexene. Reported literature yields, 24% from R$_3$B/chloramine-T, 55% from R$_3$B or R$_2$BOR'/HSA.

3-Methyl-2-butylamine hydrochloride, mp 206°–208° C. 87% yield, 99% ee, from 3-methyl-2-butene.

trans-2-Methylcyclohexylaminehydrochloride, mp 284° C. (dec), 78% yield, 99% ee, from 2-methylcyclohexene. Reported literature yields 8.5% from R$_3$B or R$_2$BOR'/chloramine, 45% from R$_3$B or R$_2$BOR'/HSA.

trans-2-Methylcyclopentylamine hydrochloride, mp 182°–186° C., 81% yield, 99% ee, from 1-methylcyclopentene. Reported literature yields, 45% from R$_3$B or R$_2$BOR'/HSA.

trans-2-Phenylcyclopentylamine hydrochloride, mp 136°–139° C., 73% yield, 99% ee, from 1-phenylcyclopentene. Reported literature yield, 45% from R$_3$B or R$_2$BOR'/HSA.

The abundant availability of both optical forms of organyldimethylboranes R*BMe$_2$, of this invention, coupled with the simple operating conditions for their conversion into chiral primary amines and easy workup, provides numerous advantages over the prior art.

While the preparation of the above compounds has been given by way of example, there are no limitations on the organo R group. R may be aliphatic, such as octyl, 2-methylpentyl, etc.; alicyclic such as cyclooctyl, cyclododecyl, etc; bicyclic and polycyclic such as norbornenyl and decalyl; steroidal; aromatic such as phenyl, naphthyl, etc.; and heterocyclic, such as 3-tetrahydropyranyl, 2-furanylethyl, 2-thiophenylethyl, pyridinyl, and the like as illustrated by Examples 12–28.

EXAMPLES 12–28

The following compounds are conveniently prepared in high yields by the method of Example 1.

3-Methyl-2-butylamine from 2-methyl-2-butene.
2-Methyl-1-pentylamine from 2-methyl-1-pentene.
2-(p-Chlorophenyl)ethylamine from p-chlorostyrene.
2-Phenylethylamine from styrene.
Cyclooctylamine from cyclooctene.
2-(4-Fluorophenyl)ethylamine from p-fluorostyrene.
2,4-Dimethyl-1-pentylamine from 2,4-dimethyl-1-pentene.
1-Hexadecylamine from 1-hexadecene.
11-Methoxyundecylamine from 11-methoxy-1-undecene.
Ethyl 11-aminoundecanoate from ethyl 10-undecanoate.
1-Octyldecylamine from 1-octadecene.
β-Naphthylamine from β-naphthalene boronic ester.
2,4,4-Trimethyl-1-pentylamine from 2,4,4-trimethyl-1-pentene.
dl-2-Methyl-2-phenylethylamine from dl-α-methylphenylethylene.
α,p-Dimethyl-2-phenylethylamine from α,p-dimethylstyrene.
2-(3-Pyridyl)-2-ethylamine from 3-vinylpyridine.
3-Aminopyrroline from 3-pyrroline.

EXAMPLES 29–38

The following additional compounds are conveniently prepared in high yields by the method of Example 1.

2-(3,4-Dimethoxyphenyl)ethylamine from 3,4-dimethoxystyrene.
1,6-Diaminohexane from 1,5-hexadiene.
3-Aminoadipic acid from 3-hexenedioic acid.
5-Aminocholesteryl acetate from cholesteryl acetate.
4-Aminocholestane from 4-cholestene.
2-(3-Tetrahydropyranyl)ethylamine from 2-vinyl tetrahydropyran.
4-Aminooxacycloheptane from 4,5-dehydrooxacycloheptene.
p-Fluorobenzeneamine from p-fluorobenzene boronic ester.
cis-Myrtanylamine of 100% ee from beta-pinene of 100% ee.
Isopinocampheylamine of 100% ee from alphapinene of 100% ee.

The above description has been given by way of illustration. It will be apparent to those skilled in the art that modifications may be made without departing from the spirit and scope of the claimed invention.

The invention claimed is:

1. A process for obtaining an optically active primary amine of essentially 100% ee in high yields represented by the formula R*NH$_2$ wherein R* is a chiral alkyl group attached to the nitrogen comprising the steps of: heating an optically active dimethylorganoborane of the formula R*BMe$_2$, wherein R* is the same alkyl group but attached to boron, in a suitable solvent with an aminating agent selected from the group consisting of NH$_2$X wherein X is halo, NH$_3$+NaOCl or CaOCl$_2$, NH$_3$+Cl$_2$, chloroamine T, and O-hydroxylamine sulfonic acid, followed by hydrolysis with aqueous base to liberate the optically active primary amine, and isolation of same.

2. The process of claim 1 wherein the aminating agent is NH$_2$X wherein X is halo.

3. The process of claim 2 wherein X is chloro.

4. The process of claim 1 wherein the aminating agent is ammonia and NaOCl or CaOCl$_2$.

5. The process of claim 1 wherein the aminating agent is NH$_3$+Cl$_2$.

6. The process of claim 1 wherein the aminating agent is chloramine-T.

7. The process of claim 1 wherein the aminating agent is hydroxylamine-O-sulfonic acid.

* * * * *